(12) United States Patent  
Heath et al.

(10) Patent No.: US 8,439,682 B1  
(45) Date of Patent: May 14, 2013

(54) SET OF ENDODONTIC INSTRUMENTS

(75) Inventors: Derek Heath, Vero Beach, FL (US); Steve Treadway, Johnson City, TN (US)

(73) Assignee: D&S Dental, LLC, Johnson City, TN (US)

( * ) Notice: Subject to any disclaimer, the term of this patent is extended or adjusted under 35 U.S.C. 154(b) by 432 days.

(21) Appl. No.: 12/398,142

(22) Filed: Mar. 4, 2009

Related U.S. Application Data

(60) Provisional application No. 61/033,685, filed on Mar. 4, 2008.

(51) Int. Cl.  
*A61C 5/02* (2006.01)

(52) U.S. Cl.  
USPC .......................................... 433/224; 433/102

(58) Field of Classification Search .................. 433/102, 433/224  
See application file for complete search history.

(56) References Cited

U.S. PATENT DOCUMENTS

| | | | |
|---|---|---|---|
| 5,106,298 A | 4/1992 | Heath et al. | |
| 5,236,357 A | 8/1993 | Randin | |
| 5,380,200 A | 1/1995 | Heath et al. | |
| 5,752,825 A | 5/1998 | Buchanan | |
| 5,820,376 A | 10/1998 | Chalifoux | |
| 5,857,852 A | 1/1999 | Garman | |
| 5,921,775 A * | 7/1999 | Buchanan | 433/102 |
| 6,162,202 A | 12/2000 | Sicurelli et al. | |
| 6,390,819 B2 | 5/2002 | Riitano | |
| 6,638,064 B1 | 10/2003 | Nance | |
| 2001/0016309 A1* | 8/2001 | Riitano | 433/224 |
| 2006/0068362 A1 | 3/2006 | Desrosiers et al. | |
| 2006/0127843 A1 | 6/2006 | Rosenblood et al. | |
| 2007/0101827 A1 | 5/2007 | Quan et al. | |

* cited by examiner

*Primary Examiner* — Todd Manahan  
*Assistant Examiner* — Michael R Ballinger  
(74) *Attorney, Agent, or Firm* — Luedeka Neely Group, PC

(57) ABSTRACT

A set of endodontic instrument adapted to remove material from walls of a root canal having a working portion with a relatively short working length. A substantially untapered nonworking portion of the instrument shaft with substantially parallel sidewalls and a diameter substantially the same as the diameter of the proximal end of the working portion extends from adjacent a proximal end of the working portion to the proximal end of the shaft. The working portions of the set of instruments have relatively small, slowly progressing taper rates.

10 Claims, 2 Drawing Sheets

SET OF ENDODONTIC INSTRUMENTS

CROSS REFERENCE TO RELATED APPLICATIONS

This application claims priority under 35 U.S.C. §119(e) to provisional application Ser. No. 61/033,685, filed Mar. 4, 2008.

FIELD

This disclosure relates to the field of endodontics. More particularly, this disclosure relates to an apparatus and method for improving and simplifying a root canal procedure.

BACKGROUND

In the field of endodontics, one of the most important and delicate procedures is that of cleaning or extirpating a diseased root canal to provide a properly dimensioned cavity while essentially maintaining the central axis of the canal for filling of the canal void and capping of the tooth. When done properly, this step enables substantially complete filling of the canal with biologically inert or restorative material without entrapping noxious tissue in the canal that could lead to failure of the therapy.

In a root canal procedure, the dentist removes diseased tissue and debris from the canal prior to filling the canal with a biologically inert or restorative filling material. In performing this procedure, the dentist must gain access to substantially the entire canal, shaping it as appropriate, in order for the procedure to be a long-term success. However, root canals often are very small in diameter, and they are sometimes quite curved. It is therefore often very difficult to gain access to the full length of the canal and to work all surfaces of the canal wall.

Many tools and techniques have been designed in an effort to enable dentists to perform the difficult task of cleaning and shaping root canals. Historically, dentists have used endodontic files to remove the soft and hard tissues in and adjacent the root canal. These endodontic files are typically made by grinding helical flutes into a working portion of a small, elongate tapered rod to create a curvilinear, abrasive file with one or more helical cutting edges. FIG. 1 is a partial cross section of a tooth 10 and supporting root structure illustrating the use of a typical fluted endodontic file 16 to carry out a standard root canal procedure. The root canal 12 of a tooth houses the circulatory and neural systems of the tooth. These enter the tooth at the apical terminus of each of its roots 20 and extend through a narrow, tapered canal system to a pulp chamber adjacent a crown portion 22 of the tooth 10. If the pulp tissue within the canal 12 becomes diseased or injured, it can cause severe pain and trauma to the tooth, sometimes necessitating extraction of the tooth. Root canal therapy involves removing the diseased tissue from the canal 12 and sealing the canal system in its entirety. If successful, root canal therapy can effectively alleviate the pain and trauma associated with the tooth so that it need not be extracted.

To perform a root canal procedure, the endodontist first drills into the tooth 10 to locate the root canal(s) 12 and then uses an endodontic file 16 to remove the decayed, injured or dead tissue from the canal 12. The endodontic files are rotated and/or reciprocated within the root canal either by hand or using a slow speed dental handpiece. The primary goal is to remove all of the decayed or injured nerve while leaving the integrity of the root canal walls relatively unaffected. Preserving the integrity of the root canal 12 is important in order to allow proper filling of the root canal void in a homogenous three dimensional manner such that leakage or communication between the root canal system and the surrounding and supporting tissues of the tooth 10 is prevented. Once as much of the diseased material as practicable is removed from the root canal 12, the canal system is sealed closed, typically by reciprocating and/or rotating a condenser instrument in the canal to urge a sealing material such as gutta-percha into the canal.

During use of an endodontic file 16 to perform root canal procedures, cutting surfaces on the instruments remove, chip, and/or abrade material from the root canal as the instrument is rotated and/or reciprocated roto-axially. The cutting surfaces are arranged along a working portion of the instrument which is typically 16 mm in length, approximately the same length as a standard root canal. This rotational movement of the cutting surfaces within the canal creates torsional and other stresses in the instrument body, which can cause a portion of an instrument to break off in the root canal when the instrument becomes over-torqued and/or fatigued.

Typical endodontic files are provided with taper rates of from 0.02 mm/mm to 0.12 mm/mm, with a taper step of 0.02 mm/mm between instruments. Due to the curved and often asymmetrical shape of many root canals, a plurality of instruments must often be employed in series, often in an order from narrow diameter, less tapered instruments to wider diameter, more tapered instruments. A wider, more tapered instrument typically would not be used first in a root canal or other similar procedure because, among other things, the more tapered instrument would not likely reach deep enough into the affected root canal before the wider end of the instrument becomes jammed in the upper hard edge of the upper portion of the canal being operated on. However, as a dentist moves between instruments having the 0.02 mm/mm taper step, the wider portion near the top of the canal still often binds in the canal. This phenomenon is sometimes referred to as "taper lock" and is preferably avoided because it can lead to tooth cracking and other similar complications.

Additionally, when an instrument is urged into the root canal in an excessively forceful manner, the shank, which may be free of cutting surfaces but is typically tapered at the same taper rate as the working portion of the instrument, may engage the upper portion of the root canal applying excessive lateral forces which can cause the tooth to split. This wedging action can also limit the ability of the working portion of the endodontic instrument to reach sufficiently into the root canal to perform its desired work on the canal wall. Further, the shank of conventional tapered endodontic instruments have a greater cross sectional diameter than the working portion and is therefore less flexible, which can interfere with an endodontist's proper maneuvering of the endodontic instrument, especially when it is necessary to roto-axially reciprocate the instrument while attempting to work deeper portions of a canal wall.

Accordingly, there is a need for an endodontic instrument design and method for use that will minimize the wedging action caused by the shank of typical endodontic instruments, decrease the number of instruments required to successfully carryout the procedure, and increase the flexibility of the shank of the endodontic instrument(s).

SUMMARY

The above and other needs are met by a set of endodontic instrument adapted to remove material from walls of a root canal. Each instrument in the set includes an elongate shaft having a proximal end adapted to be gripped by the hand of a user or mechanically coupled to a dental handpiece to be selectively rotatably and axially driven within a root canal of a tooth and a distal end spaced from the proximal end by the length of the instrument. A portion of the shaft adjacent the distal end of the instrument defines a working portion with a relatively short working length of about 10 mm having cutting edges adapted to extirpate material from a root canal. A substantially untapered nonworking portion of the shaft with substantially parallel sidewalls and a diameter substantially the same as the diameter of the proximal end of the working portion extends from adjacent a proximal end of the working portion to the proximal end of the shaft. The working portions of the set of instruments have relatively small taper rates slowly progressing in 0.01 mm/mm increments from about 0.01 mm/mm for the least tapered instrument in the set to about 0.04 mm/mm for the most tapered instrument in the set.

BRIEF DESCRIPTION OF THE DRAWINGS

Further features, aspects, and advantages of the present disclosure will become better understood by reference to the following detailed description, appended claims, and accompanying figures, wherein elements are not necessarily to scale so as to more clearly show the details, wherein like reference numbers indicate like elements throughout the several views, and wherein:

DETAILED DESCRIPTION

Figure 1:
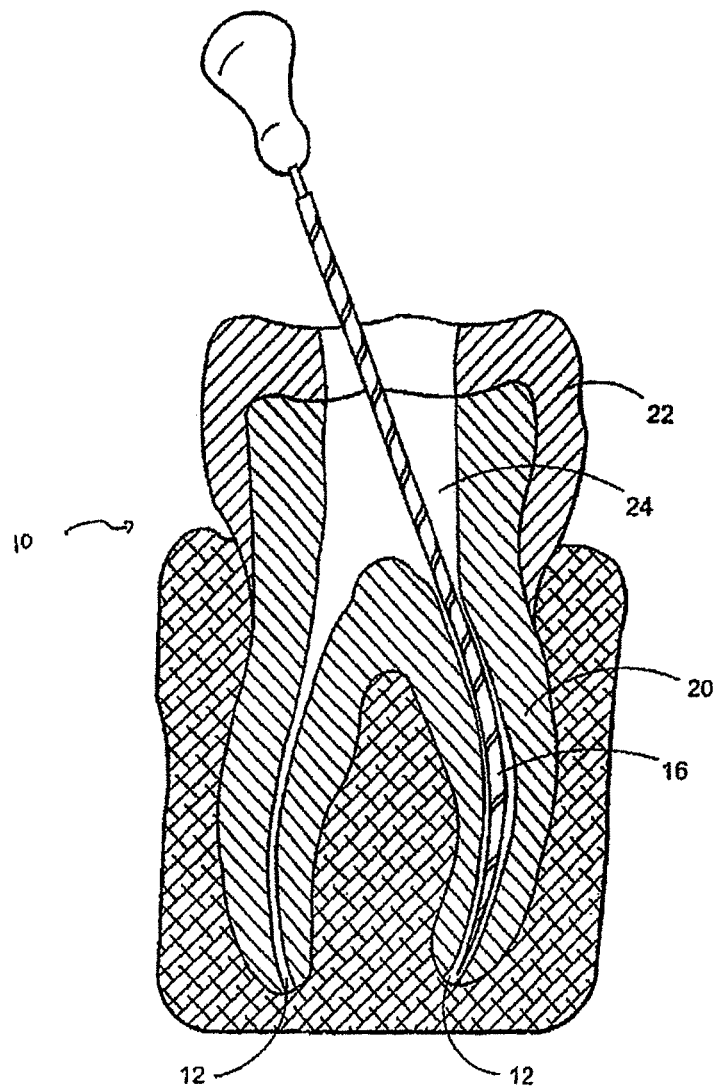
FIG. 1 is a section view of a tooth and root structure illustrating the use of a typical endodontic instrument for performing a typical root canal procedure.
Figure 2:
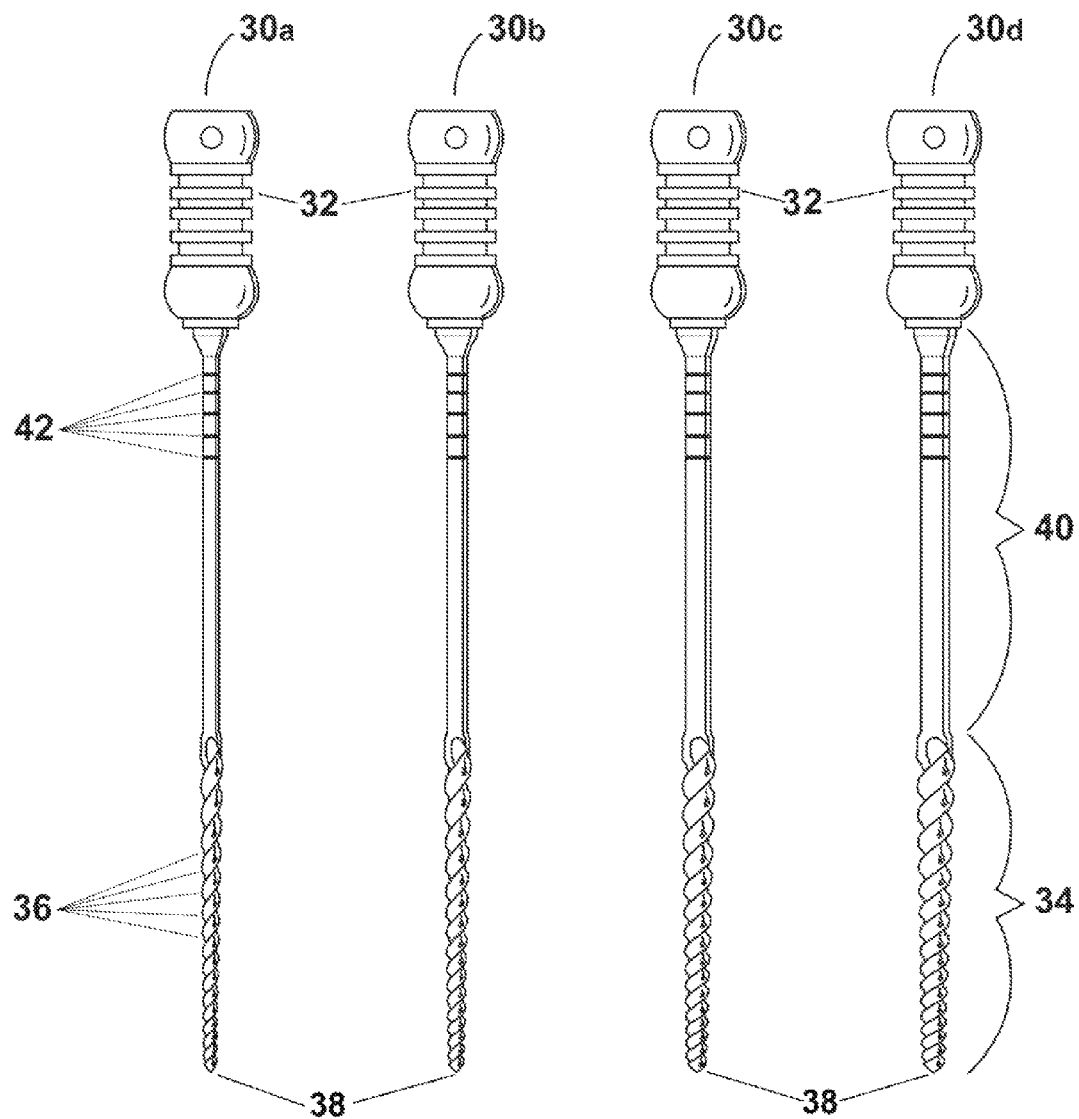
FIG. 2 shows a set of endodontic instruments according to one embodiment of the invention.

FIG. 2 shows a plurality of endodontic instruments 30a-30d according to one preferred embodiment of the present invention. The elongate instruments are preferably formed from an elongate rod of stainless steel or nickel-titanium alloy having a diameter of from about 0.3 and to about 1.6 mm, although the rod may have a larger or smaller diameter as needed. In suitable embodiments, rods made from other suitable metals and/or alloys may be used. The proximal end of the instrument preferably includes a handle 32 to facilitate hand manipulation of a file or a fitting portion (not shown) for mating with the chuck of a dental handpiece. The fitting portion may include a generally I-shaped flat side which defines a step and a generally semicircular disk above and adjacent to a generally semi-circular groove. Such a fitting is typical of those employed in the dental industry for connecting or interfacing a dental tool with dental drill or handpiece. In other embodiments, the fitting may be modified for connecting or interfacing with non-typical or other types of dental tools. Thus, the instrument may either be used by manipulating the instrument manually in a rotating or reciprocating action, or the instrument may be manipulated by attaching the fitting portion of the instrument to a motorized handpiece for effecting more rapid removal of tissue from the root canal, as desired.

The instrument includes a working portion 34 preferably extending from adjacent a distal tip end of the instrument to adjacent a shank portion 40. The shank portion 40 may have calibration markings 42 to assist a dentist in determining the depth of the instrument into the root canal. The tip 38 of the instrument may assume any number of a variety of possible configurations known in the art (e.g., chisel, cone, bullet, multi-faceted and/or the like). The working portion includes a plurality of cutting surfaces, which are preferably continuous helical cutting surfaces 36. Alternately, the cutting surfaces could be discontinuous or the cutting surfaces may be non-helical angled corners extending along a portion of the length of a polygonal, fluteless rod, barbed cutting surfaces, or other cutting and/or abrading surfaces known in the art.

The applicant has discovered that a set of instruments having a combination of a relatively short working portion and an otherwise standard length and with a nontapered shank portion where the instruments in the set gradually increase in taper provides a beneficial and what is believed to be a synergistic effect in reducing taper lock and resulting breakage from too rapid of an increase in taper step and unnecessarily long working portions found in typical endodontic files and also limiting undesirable lateral transposition of the axis of a canal from the original canal axis. In the instruments of the present invention, the length of the working portion 34 has been reduced from the standard 16 mm length results. This provides an instrument which has limited torsional stress when rotated in the root canal, because the cutting surfaces of such an instrument have a smaller area of engagement with the walls of a canal. Accordingly, such instruments are less likely to become fatigued and break off into a canal during use. The length of the working portion 34 preferably ranges from about 6 mm to about 12 mm, and is most preferably about 10 mm.

The set of instruments preferably includes four instruments 30a-30d each having substantially the same overall length and working portions having the same length, although about 3 to about 5 instruments may be used in the set of the present invention. Additionally, the distal ends of the working portion of the instruments preferably have the same diameter. The distal end diameter is preferably from about 0.15 mm to about 0.6 mm. Each instrument in the set has a working portion with a different taper rate. The taper rates preferably range from about 0.01 mm/mm to about 0.04 mm/mm, although other relatively small taper rates of up to about 0.06 mm/mm are contemplated. Larger taper rates as typically used in root canal procedures are believed to result in a greater likelihood of taper lock due to the wider portion adjacent the proximal end of the working portion binding in the upper portion of the canal.

Additionally, the instruments in the set preferably have working portions of progressively increasing taper rates from the instrument with the smallest taper to the instrument with the largest taper in 0.01 mm/mm increments. This slowly progressing taper limits the taper lock which can be found in standard instruments with tapers steps of 0.02 mm/mm between instruments in a set.

In order to allow the instruments to reach into the canal a sufficient distance to work the areas of the canal adjacent the apical canal, the instruments 30 are preferably provided with an elongate shank 40 substantially free of cutting surfaces with a length of from about 5 mm to about 30 mm, most preferably about 11 to about 21 mm. The overall length of the instrument preferably has a length similar to standard endodontic instruments of from about 20 mm to about 35 mm. The diameter of the shank 40 at its distal end is preferably substantially the same as the diameter of the proximal end of the working portion 34. The diameter of the shank preferably ranges from about 0.25 mm to about 1.0 mm. The shank is preferably substantially cylindrical along its length. The constant diameter shank having the same diameter as the proximal end of the working portion has been found to limit the shank's engagement of upper portions of a root canal and to provide more uniform flexibility along the entire length of the instrument when the instrument is used to work deeper portions of the canal.

A dentist may use the set of endodontic instruments 30a-30d to work a root canal. The dentist preferably uses a first instrument with a narrow taper of about 0.01 to work the portion of the root canal nearest the apical portion of the canal. The dentist may then progressively use other instruments in the set at a taper step of 0.01 mm/mm to work portions farther towards the top of the canal, while avoiding the taper lock which can be present when using sets of typical instruments with larger taper steps between instruments. The relatively small taper of the set of instruments of the present invention and the constant diameter shank results in an instrument which does not change in diameter as significantly as prior instruments with larger tapers and tapered shanks, thereby resulting in an instrument which is more flexible and more uniformly flexible along its length. This provides the dentist with greater control of the instrument and limits lateral transposition of the canal. Additionally, the small progression of taper rates, the short working length of the instrument, the small taper, and the nontapered shanks are believed to synergistically limit the torque and resulting breakage and taper lock of the instruments within the canal. In certain embodiments, the dentist may use multiple sets of instruments of the present invention in root canal therapies, where each set has a different distal tip diameter.

Endodontic instruments of the present invention may be manufactured by permanently twisting a tapered rod of substantially triangular or square cross section, where the apices of the triangular or square cross section thus formed cutting edges which spiral along the length of the instrument. However, it is preferred to manufacture the endodontic instruments by a machining process, wherein a cylindrical rod of stainless steel or nickel titanium alloy is first cut into blanks of about two inches in length. The rod may then be tapered in accordance with the present invention by machining the rod in a centerless grinding machine. Helical flutes may then be machined on the distal end portion of the rod, by moving the blank past a rotating grinding wheel and while the blank is rotated to impart the desired helical configuration to the flutes. A cutting edge is thus formed along the edges of each flute, and a helical land may be formed between the spiral flutes. In other embodiments, non-helical cutting surfaces, notches, and/or barbs may be machined on the distal end portion of the rod according to manufacturing methods know in the art.

The foregoing description of preferred embodiments for this disclosure has been presented for purposes of illustration and description. The disclosure is not intended to be exhaustive or to limit the various embodiments to the precise form disclosed. Other modifications or variations are possible in light of the above teachings. The embodiments are chosen and described in an effort to provide the best illustrations of the principles of the underlying concepts and their practical application, and to thereby enable one of ordinary skill in the art to utilize the various embodiments with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A set of endodontic instruments adapted to remove material from walls of a root canal, each instrument comprising an elongate shaft having a proximal end adjacent a handle adapted to be gripped by the hand of a user or a fitting for mechanically coupling to a dental handpiece to be selectively rotatably and axially driven within a root canal of a tooth and a distal end spaced from the proximal end by the length of the instrument, wherein a portion of the shaft adjacent the distal end of the instrument defines a working portion with a short working length of 10 mm having cutting edges adapted to extirpate material from a root canal, and an untapered nonworking portion of the shaft having a diameter the same as the diameter of the proximal end of the working portion wherein such untapered nonworking portion extends from adjacent a proximal end of the working portion to the proximal end of the shaft, wherein the working portions of the set of instruments have small taper rates slowly progressing in 0.01 mm/mm increments from 0.01 mm/mm for the least tapered instrument in the set to 0.04 mm/mm for the most tapered instrument in the set, and wherein the working portion of all of the instruments in the set has a diameter at the distal end which is the same.

2. The set of endodontic instruments of claim 1, wherein the instruments have a length from the proximal end to the distal end of the shaft of from 21 mm to 31 mm.

3. The set of endodontic instruments of claim 1, wherein the lengths of the instruments in the set are the same.

4. The set of endodontic instruments of claim 1, wherein the nonworking portion of the instruments have a diameter of from 0.25 mm to 1 mm.

5. The set of endodontic instruments of claim 1, wherein the working portion of the instruments adjacent the distal end of the instrument has a diameter of from 0.15 mm to 0.6 mm.

6. The set of endodontic instruments of claim 1, wherein the working portion of the instruments comprise helically fluted cutting surfaces for removing material from the walls of a root canal.

7. The set of endodontic instruments of claim 1, wherein the instrument shafts comprise a stainless steel material.

8. The set of endodontic instruments of claim 1, wherein the instrument shafts comprise a nickel titanium alloy.

9. A set of endodontic instruments adapted to remove material from walls of a root canal, each instrument comprising an elongate shaft having a proximal end adjacent a handle adapted to be gripped by the hand of a user or a fitting for mechanically coupling to a dental handpiece to be selectively rotatably and axially driven within a root canal of a tooth and a distal end spaced from the proximal end by the length of the instrument, wherein a portion of the shaft adjacent the distal end of the instrument defines a working portion with a short working length of 6 mm to 12 mm having cutting edges adapted to extirpate material from a root canal, and an untapered nonworking portion of the shaft having a diameter the same as the diameter of the proximal end of the working portion wherein such untapered nonworking portion extends from adjacent a proximal end of the working portion to the proximal end of the shaft, wherein the working portions of the set of instruments have small taper rates slowly progressing in 0.01 mm/mm increments from the least tapered instrument in the set to the most tapered instrument in the set, and further wherein the length of each instrument in the set is the same and the working portion of each instrument in the set has a diameter at the distal end which is the same.

10. A method for removing material from walls of a root canal using a set of endodontic instruments, each instrument comprising an elongate shaft having a proximal end adjacent a handle adapted to be gripped by the hand of a user or a fitting for mechanically coupling to a dental handpiece to be selectively rotatably and axially driven within a root canal of a tooth and a distal end spaced from the proximal end by the length of the instrument, wherein at least a portion of the shaft adjacent the distal end of the instrument defines a working portion with a short working length of 10 mm having cutting edges adapted to extirpate material from a root canal, and an untapered nonworking portion of the shaft having a diameter the same as the diameter of the proximal end of the working portion wherein such untapered nonworking portion extends from adjacent a proximal end of the working portion to the proximal end of the shaft, wherein the working portions of the set of instruments have small taper rates slowly progressing in 0.01 mm/mm increments from 0.01 mm/mm for the least tapered instrument in the set to 0.04 mm/mm for the most tapered instrument in the set, and wherein the working portion of all of the instruments in the set has a diameter at the distal end which is the same, the method comprising working the root canal with an instrument from the set having a working portion with a first taper rate and then working the root canal with an instrument having a working portion with a second taper rate that is 0.01 mm/mm greater than the first taper rate.

* * * * *